(12) United States Patent
Kim et al.

(10) Patent No.: US 8,907,290 B2
(45) Date of Patent: Dec. 9, 2014

(54) METHODS AND SYSTEMS FOR GAIN CALIBRATION OF GAMMA RAY DETECTORS

(75) Inventors: Chang Lyong Kim, Brookfield, WI (US); David Leo McDaniel, Dousman, WI (US); James Lindgren Malaney, Brookfield, WI (US); William Todd Peterson, Sussex, WI (US); Vi-Hoa Tran, Pewaukee, WI (US); Ashwin Ashok Wagadarikar, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 250 days.

(21) Appl. No.: 13/492,439

(22) Filed: Jun. 8, 2012

(65) Prior Publication Data

US 2013/0327932 A1    Dec. 12, 2013

(51) Int. Cl.
*G01T 1/24* (2006.01)

(52) U.S. Cl.
USPC .................................................... 250/363.03

(58) Field of Classification Search
CPC ............................ G01T 1/248; G01T 7/005
USPC ...................................................... 250/363.03
See application file for complete search history.

(56) References Cited

U.S. PATENT DOCUMENTS

| 5,677,536 | A | 10/1997 | Vickers |
| 6,624,422 | B2 | 9/2003 | Williams et al. |
| 6,858,850 | B2 | 2/2005 | Williams et al. |
| 7,723,694 | B2 * | 5/2010 | Frach et al. ............... 250/370.11 |
| 2008/0251709 | A1 | 10/2008 | Cooke et al. |
| 2013/0009266 | A1 * | 1/2013 | Sato et al. ..................... 257/438 |

\* cited by examiner

*Primary Examiner* — Constantine Hannaher
(74) *Attorney, Agent, or Firm* — Dean D. Small; The Small Patent Law Group

(57) ABSTRACT

A method for gain calibration of a gamma ray detector includes measuring signals generated by one or more light sensors of a gamma ray detector, generating one or more derived curves using the measured signals as a function of bias voltage and identifying a transition point in the one or more derived curves. The method also includes determining a breakdown voltage of the one or more light sensors using the identified transition point and setting a bias of the one or more light sensors based on the determined breakdown voltage.

25 Claims, 7 Drawing Sheets

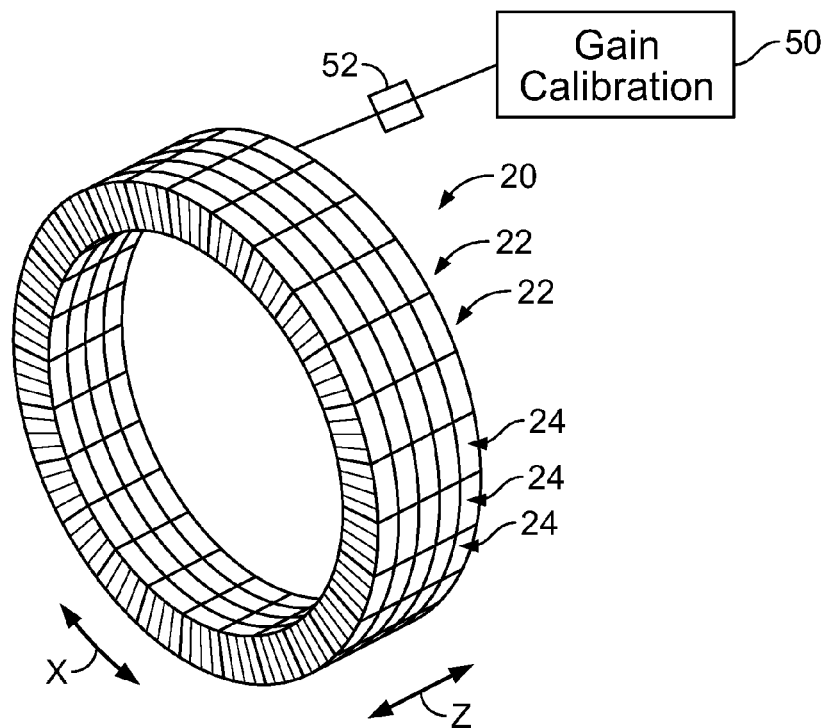
FIG. 1
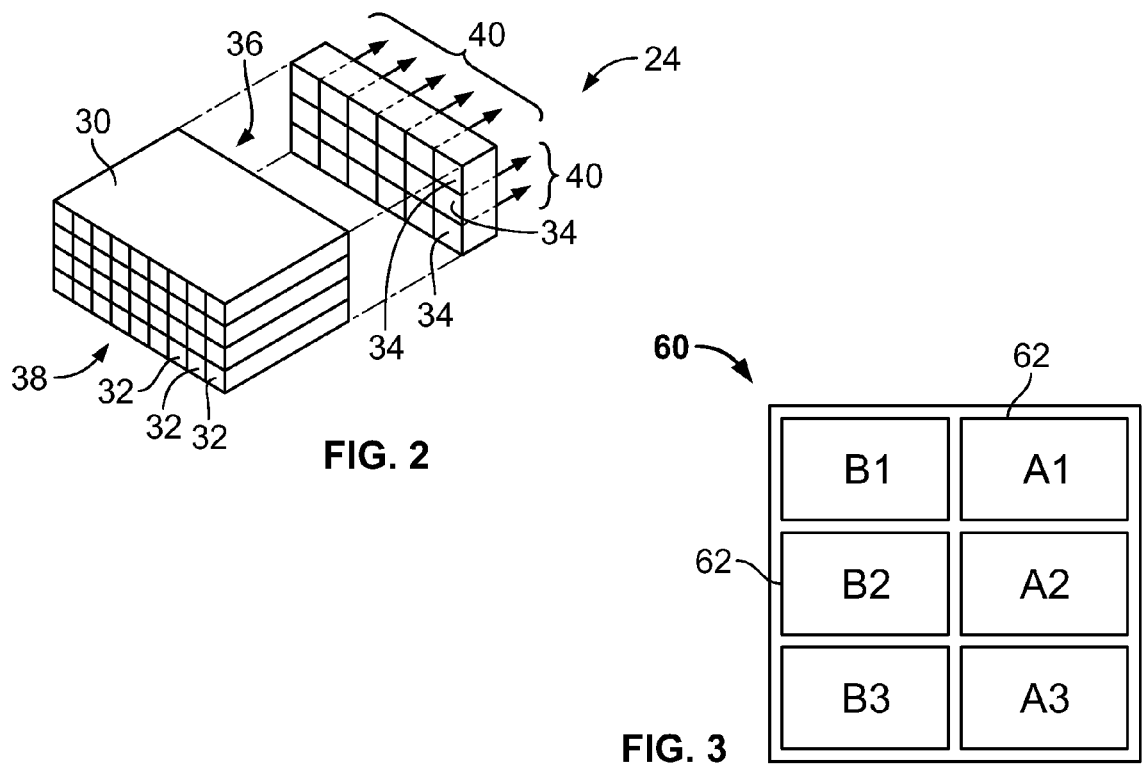
FIG. 2
FIG. 3

METHODS AND SYSTEMS FOR GAIN CALIBRATION OF GAMMA RAY DETECTORS

BACKGROUND OF THE INVENTION

This subject matter disclosed herein relates generally to gamma ray detectors, and more particularly, to systems and methods for gain calibration of gamma ray detectors.

Gamma ray detectors may be used in different applications, such as in Positron Emission Tomography (PET) systems. PET systems perform nuclear medicine imaging that generates a three-dimensional image or picture of functional processes within a body. For example, a PET system generates images that represent the distribution of positron-emitting nuclides within the body of a patient. When a positron interacts with an electron by annihilation, the entire mass of the positron-electron pair is converted into two 511 keV photons. The photons are emitted in opposite directions along a line of response. The annihilation photons are detected by detectors that are placed along the line of response on a detector ring. When these photons arrive and are detected at the detector elements at the same time, this is referred to as coincidence. An image is then generated based on the acquired image data that includes the annihilation photon detection information.

In PET systems, the gamma rays are detected by a scintillator in the scanning system, creating light that is detected by a photo-sensor (e.g., a photomultiplier tube (PMT), a silicon avalanche photodiode or a solid state photomultiplier). PET detectors based on vacuum photomultiplier photo-sensors require gain/energy calibration in order to properly operate. When using a small crystal array (e.g., 4×4 array) on solid state photomultiplier based PET detectors with multi-anodes (e.g., six anodes in a 2×3 array), it is often difficult to define reference crystals as the arrangement is very sensitive to the relative positioning of crystals over the anodes. Additionally, as the number of anodes increases, for example when six or more anodes are used, it is more difficult to apply conventional PET iterative algorithms to perform gain and energy calibration. For example, the processes may be more complex and time consuming.

For the case of a one-to-one coupling between the photosensor of solid state photomultiplier based PET detectors and the detector crystal (e.g., a Cerium doped Lutetium Yttrium Orthosilicate (LYSO) crystal), the 511 keV energy peak or known LYSO intrinsic background peaks can be used for calibration. However, in some designs, for example, a light-sharing block design among multiple anodes, this is not possible. Additionally, typical gain calibration for solid state photomultiplier based PET detectors may be performed by measuring a single photon pulse height when dark counts/current is small. To perform these measurements, a very high gain/low noise amplifier is needed. However, when the size of the photo-sensors in these solid state photomultiplier based PET detectors increases, for example, larger than 3×3 mm² or when generating greater than 1 million dark counts per second, these measurements also cannot be performed because the single photon pulse cannot be identified properly due to count pileup. For example, in a 4×6 mm² device, more than 10 million counts per second may be detected.

Thus, known processes for gain or energy calibration may not work satisfactorily for some configurations of gamma detectors, such as gamma detectors used in combination with photo-sensors, such as in solid state photomultiplier based PET detectors.

BRIEF DESCRIPTION OF THE INVENTION

In one embodiment, a method for calibrating a gamma ray detector is provided. The method includes measuring signals generated by one or more light sensors of a gamma ray detector, generating one or more derived curves using the measured signals as a function of bias voltage and identifying a transition point in the one or more derived curves. The method also includes determining a breakdown voltage of the one or more light sensors using the identified transition point and setting a bias of the one or more light sensors based on the determined breakdown voltage.

In another embodiment, a Position Emission Tomography (PET) system is provided that includes a plurality of gamma ray detector elements configured to acquire scan data, wherein the detector elements have scintillator crystals with a plurality of lights sensors. The PET system also includes a processor configured to measure signals generated by one or more of the plurality light sensors of the gamma ray detector, generate one or more derived curves using the measured signals as a function of bias voltage, identify a transition point in the one or more derived curves, determine a breakdown voltage of the one or more of the plurality of light sensors using the identified transition point, and set a bias of one or more of the plurality of light sensors based on the determined breakdown voltage.

BRIEF DESCRIPTION OF THE DRAWINGS

FIG. 1 is a perspective view of a positron emission tomography (PET) detector assembly in accordance with an embodiment.

FIG. 2 is a perspective view of a detector unit formed in accordance with an embodiment.

FIG. 3 is a schematic block diagram of Silicon photomultipliers (SIPMs) in accordance with an embodiment.

DETAILED DESCRIPTION OF THE INVENTION

Figure 4:
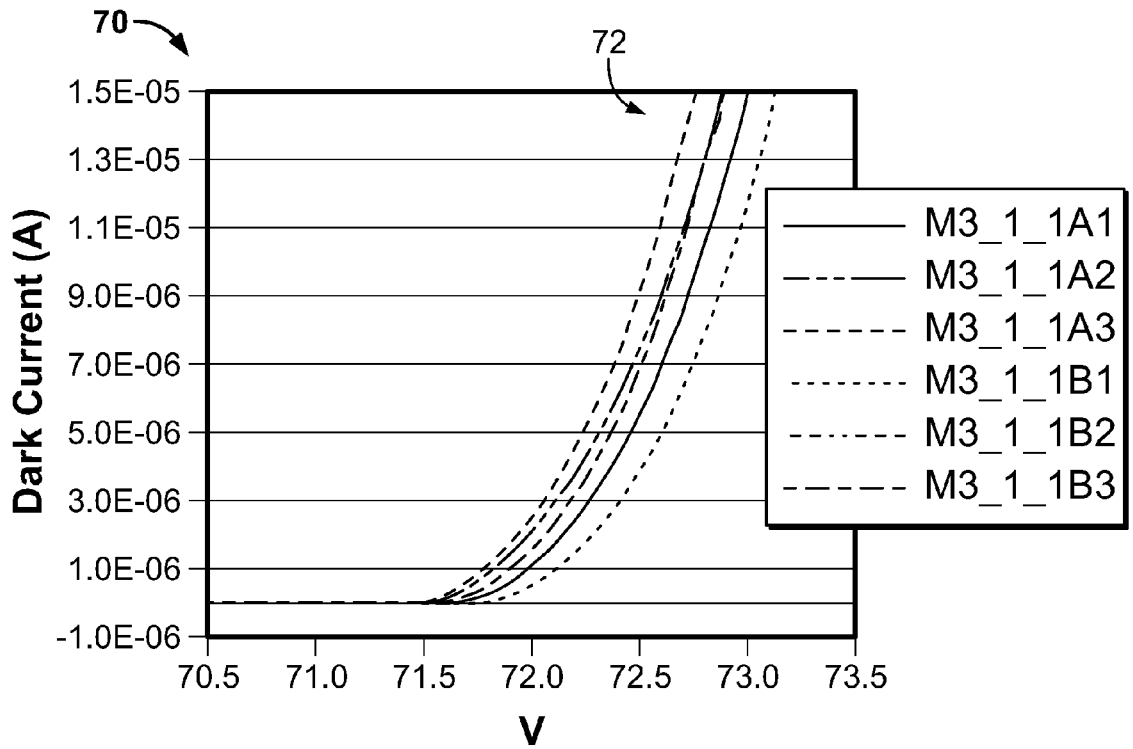
FIG. 4 is a graph of dark currents in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for performing calibration for gamma ray detectors (e.g., energy and gain calibration), such as for Positron Emission Tomography (PET) systems. Various embodiments use the current including from dark currents, which may also include any signal added from natural background radiation or external signal, to measure the breakdown voltage of photo-sensors of the gamma detectors, which in some embodiments are Silicon photomultipliers (SIPMs). A gain is then adjusted based on the measurement. For example, an increase in current would be presented as a baseline shift or average peak shift in the sample electronics. At least one technical effect of various embodiments is to provide the gain and/or energy calibration with SIPMs having multiple anodes and that may be provided in a light-sharing block design.

Various embodiments may be used in combination with gamma ray detectors (also referred to herein as gamma detectors) in a PET system having a PET detector assembly 20 shown in perspective view in FIG. 1. However, it should be appreciated that the gamma detectors and various embodiments may be implemented in different types of imaging and non-imaging systems. In the illustrated embodiment, the PET detector assembly 20 is coupled to a gain calibration module 50 (or assembly) that includes electronics for processing received current measurements, including dark currents, to calibrate photomultiplier photo-sensors, such as SIPMs of the PET detector assembly 20. For example, the gain calibration module 50 may receive one or more measurement signals from a plurality of application specific integrated circuits (ASICs) connected to the PET detector assembly 20. Thus, the PET detector ring assembly 20 may be utilized to provide signals to the gain calibration module 50.

In various embodiments, the PET detector assembly 20 includes a plurality of detector modules 22 that are arranged in a ring to form the PET detector ring assembly 20. Each detector module 22 is assembled from a plurality of detector units 24. Thus, a plurality of detector units 24 is assembled to form a single detector module 22, and a plurality of detector modules 22 is assembled to form the detector ring assembly 20. In one embodiment, the detector assembly 20 includes twenty-eight detector modules 22 that are coupled together such that the detector assembly 20 has a ring shape. In some embodiments, each detector module 22 includes twenty detector units 24 that are arranged in a 4×5 matrix. It should be realized that the quantity of detector modules 22 utilized to form the detector assembly 20 is exemplary, and that the detector assembly 20 may have more than or fewer than twenty-eight detector modules 22. Moreover, it should be realized that quantity of detector units 24 utilized to form each detector module 22 is exemplary, and that the detector module 22 may have more than or fewer than twenty detector units 24.

FIG. 2 is a perspective view of an exemplary detector unit 24 that may form a portion of the detector module 22 shown in FIG. 1. In various embodiments, the detector unit 24 includes a scintillator block 30 having one or more scintillator crystals 32 that are arranged along an x-axis and a z-axis. In one embodiment, the scintillator block 30 has thirty-six crystals 32 that are arranged in a 4×9 matrix. However, it should be realized that the scintillator block 30 may have fewer than or more than thirty-six crystals 32, and that the crystals 32 may be arranged in a matrix of any suitable size. It also should be noted that the scintillator crystals 32 may be formed from any suitable material such as bismuth germinate (BGO), Cerium-doped Lutetium Yttrium Orthosilicate (LYSO) or Gadolinium Oxyorthosilicate (GSO), among others.

The detector unit 24 also includes a plurality of light sensors 34, illustrated as a plurality of photosensors, which may be any suitable photo-detectors that sense or detect light or other electromagnetic energy. In the illustrated embodiment, the light sensors 34 are SIPMs. The plurality of light sensors 34 are coupled at an end of the scintillator block 30 opposite a detector face 38. The surfaces of the crystal block 30 not coupled to the light sensors 34 are covered with a reflective layer such as Teflon, TiO2 load Epoxy, or a spectral reflector. It should be noted that in some embodiments, a reflector or reflective material may be placed between some crystals in the crystal block 30.

In various embodiments, the detector unit 24 has eighteen light sensors 34 on each end of the scintillator block 30 that are arranged in a 3×6 matrix. However, it should be realized that the detector unit 24 may have fewer than or more than eighteen light sensors 34 and that the light sensors 34 may be arranged in a matrix of any suitable size. For example, some embodiments include 36, 54 or 100 crystals 32 having corresponding light sensors 34 that are arranged in a 6×6 matrix, 9×6 matrix or 10×10 matrix, respectively. It should be noted that in various embodiments, a one-to-one coupling between the light sensor 34 (e.g., a photosensor) and the crystal 32 is not provided, such that there is a one-to-multiple coupling between the light sensor 34 and the crystal 32. However, in other embodiments, a one-to-one coupling between the light sensor 34 (e.g., a photosensor) and the crystal 32 may be provided. Also, the light sensors 34 may have a different size or shape. In some embodiments, the light sensors 34 are larger than 3×3 mm². However, in other embodiments, larger or smaller light sensors 34 may be used, such as 4×6 mm² light sensors 34.

In one embodiment, the light sensors 34 are avalanche photodiodes that are connected in parallel and operated above a breakdown voltage in a Geiger mode. For example, the light sensors 34 may be SIPMs in various embodiments that are configured as single photon sensitive devices formed from an avalanche photodiode array on a silicon substrate. However, it should be noted that the light sensors 34 may be any type of light sensor, wherein a normalized rate of change of dark current versus bias voltage has a peak, and wherein gain can be determined from the applied voltage and the position of this peak.

In operation, the scintillator crystals 32 convert the energy, deposited by a gamma ray impinging on the scintillator crystal 32, into visible (or near-UV) light photons. The photons are then converted to electrical analog signals by the light sensors 34. More specifically, when a gamma ray impinges on any one of the scintillator crystals 32 in a detector unit 24, the scintillator detecting the gamma ray converts the energy of the gamma ray into visible light that is detected by the light sensors 34 in the detector unit 24. Thus, in the exemplary embodiment, each detector unit 24 is configured to output "n" analog signals 40.

In operation, in order to achieve proper gain, the light sensors 34, for example, the SIPMs are biased at an operating voltage above the breakdown voltage of the SIPM in a Geiger mode. FIG. 3 illustrates an array 60 of SIPMs 62 (illustrated as a 2×3 array) in accordance with an embodiment. Each of the SIPMs 62 represents a separate anode and each of the SIPMs 62 are biased, namely, has a bias voltage applied thereto. The graph 70 of FIG. 4 shows I-V curves 72 corresponding to each of the anodes, namely each of the SIPMs 62. It should be noted that the horizontal axis in the graph 70 represents voltage and the vertical axis represents dark current. As can be seen, the transition point in each of the curves 72 is about 71.5 volts, representing the breakdown voltage. However, as described in more detail herein, more than one transition point may be present. As can also be seen, the breakdown voltage of each of the SIPMs 62 is slightly different.

The difference between the operating voltage and the breakdown voltage is referred to as over-voltage and is proportional to gain. In particular, Gain=Over-Voltage×Capacitance. Accordingly, this characteristic indicates that below the breakdown voltage, there are almost no dark currents and above the breakdown voltage, the Gain increases with Over-Voltage, as the Capacitance of the SIPM 62 (e.g., each individual anode or cell) is fixed. Thus, the I-V curves 72 (as illustrated in FIG. 4) should generally have a linear increase from the breakdown voltage and higher, however, as can be seen in the graph 70 (shown in FIG. 4), the I-V curves 72 have an exponential shape as a result of the higher probability of avalanche for free electrons, increased depletion region, optical cross-talk among microcells, and after pulses, which are not linear to bias.

Accordingly, the dark currents or total currents may be defined as follows:

$$\text{Dark Currents (or Total Current)} = f(\text{Gain}) \text{ or } f(\text{Over-Voltage})$$

In various embodiments, the characteristic shape of the I-V curves 72 for the dark currents is used to calculate the breakdown voltage that is then used in gain calibration by the gain calibration module 50 (shown in FIG. 1). In various embodiments, once the breakdown voltage is determined, the same over-voltage is applied as a bias to each of the SIPMs 62.

In various embodiments, one or more of the I-V curves 72 may be obtained from the change in the baseline of the output signal from the readout electronics while sweeping the bias voltage over the breakdown voltage. In various embodiments, the I-V curves 72 may be obtained from a combination of signals from the natural background radiation or external radiation sources and the dark current. In these embodiments, the change in the time averaged output signal of the readout electronics is measured as a function of the applied bias voltage. Since the signal generated by the SIPM 62 due to a photon is the same signal generated by a dark count event, the shape of the I-V curve generated from the time average signal will be substantially the same as the shape of the I-V curve generated from the change in the baseline of the output signal. The time averaged signal out of the readout electronics will be larger than the baseline of that signal. Therefore, for a given change in the bias voltage, the change in the time average signal will be larger than the change in the baseline of the signal. Therefore, when the dark current from SIPM 62 is very low, using the time averaged signal value may give a more accurate measurement of the I-V curve.

Various embodiments provide gain calibration, for example, for SIPM based PET detectors. The gain calibration module 50 may include interface electronics 52 that allow for the measurement of a baseline signal versus an applied voltage as subsets of the SIPM anodes are enabled. Additionally, in various embodiments, the gain calibration module 50 also calculates the breakdown voltage from the obtained dark current/baseline signal dependence on bias. In operation, online calibration and/or continuous monitoring of gain may be provided.

Figure 5:
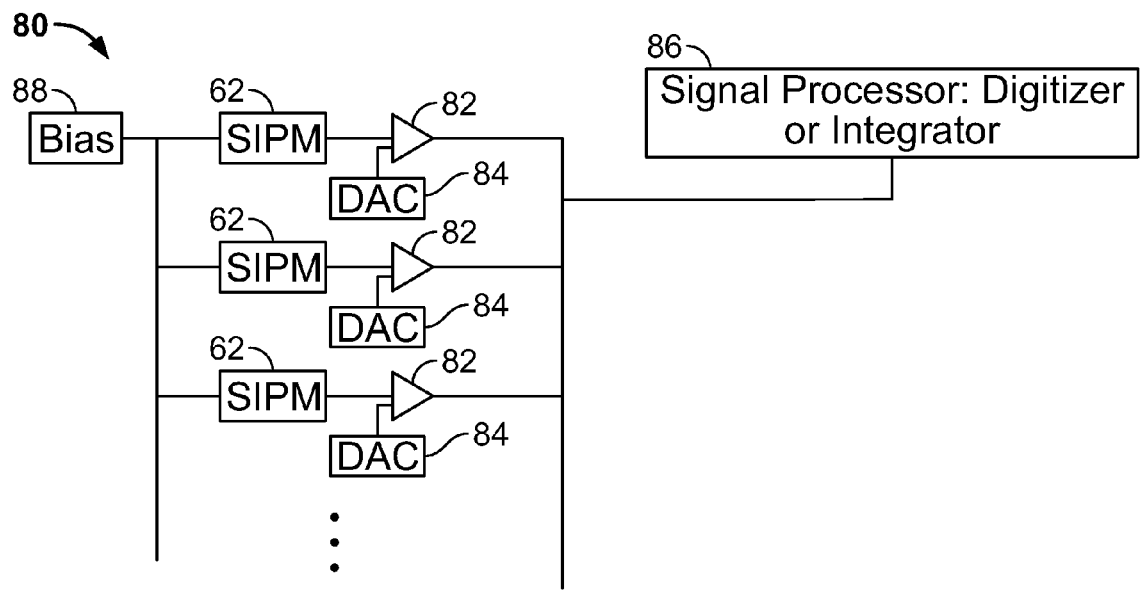
FIG. 5 is a block diagram of readout electronics in accordance with an embodiment.

One embodiment of readout electronics 80 is shown in FIG. 5. The readout electronics 80 include a plurality of buffer amplifiers 82. In the illustrated embodiment, one buffer amplifier 82 is connected to a respective SIPM 62 such that the output of the SIPM 62, which in one embodiment is a current, is provided as in input to the buffer amplifier 82. Additionally, a digital to analog converter (DAC) 84 is also connected to an input of the buffer amplifier 82, which is provided with an anode bias control signal in some embodiments. The outputs of the buffer amplifiers 82 are connected to a signal processor 86, which may include a digitizer, integrator and/or comparator. A bias source 88 is also connected to each of the SIPMs 62 to provide a cathode bias voltage as described in more detail herein.

In operation, the bias voltage from the cathode bias source 88 and the anode bias from the DAC 84 are used to adjust the bias to the SIPMs 62. By adjusting the cathode bias, namely the bias applied to the SIPMs 62, and/or the anode bias from the DACs 84, the I-V curve, for example the I-V curves 72 (shown in FIG. 4) for the SIPMs 62 can be measured. It should be noted that in some embodiments the measured current (I) from the SIPMs 62 represents the current from the dark pulses and the current generated by photons produced in the scintillation crystals 32.

Figure 8:
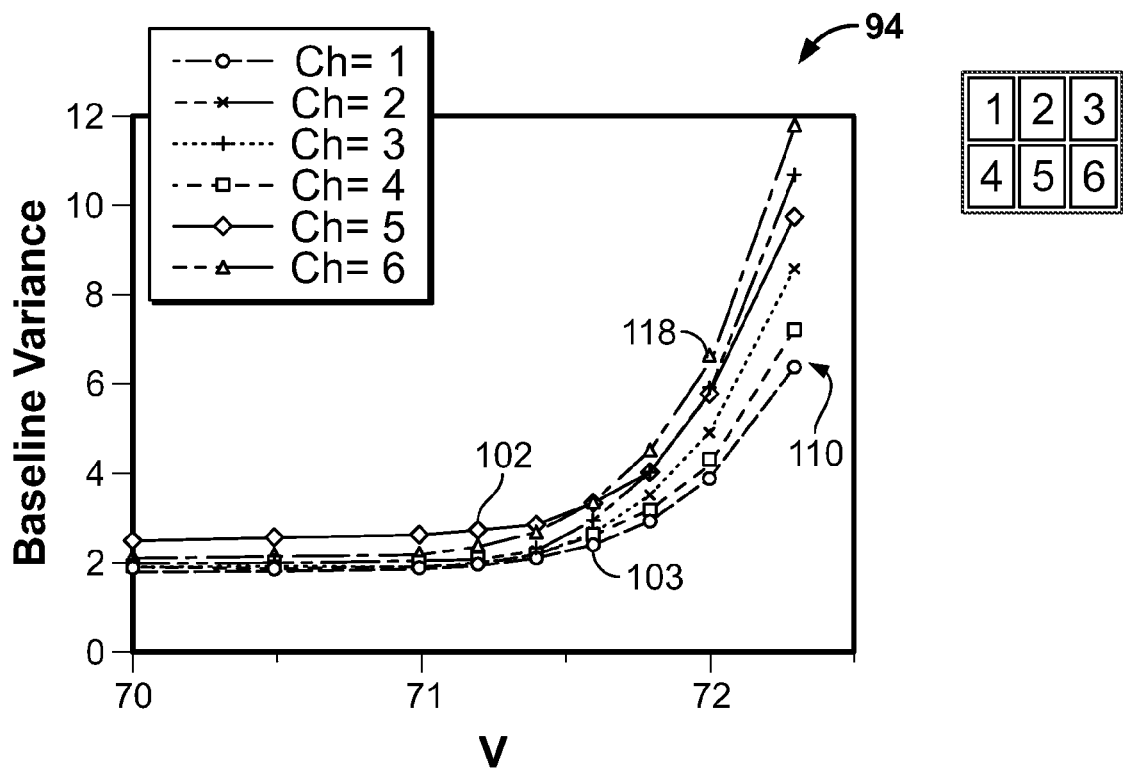
Figure 9:
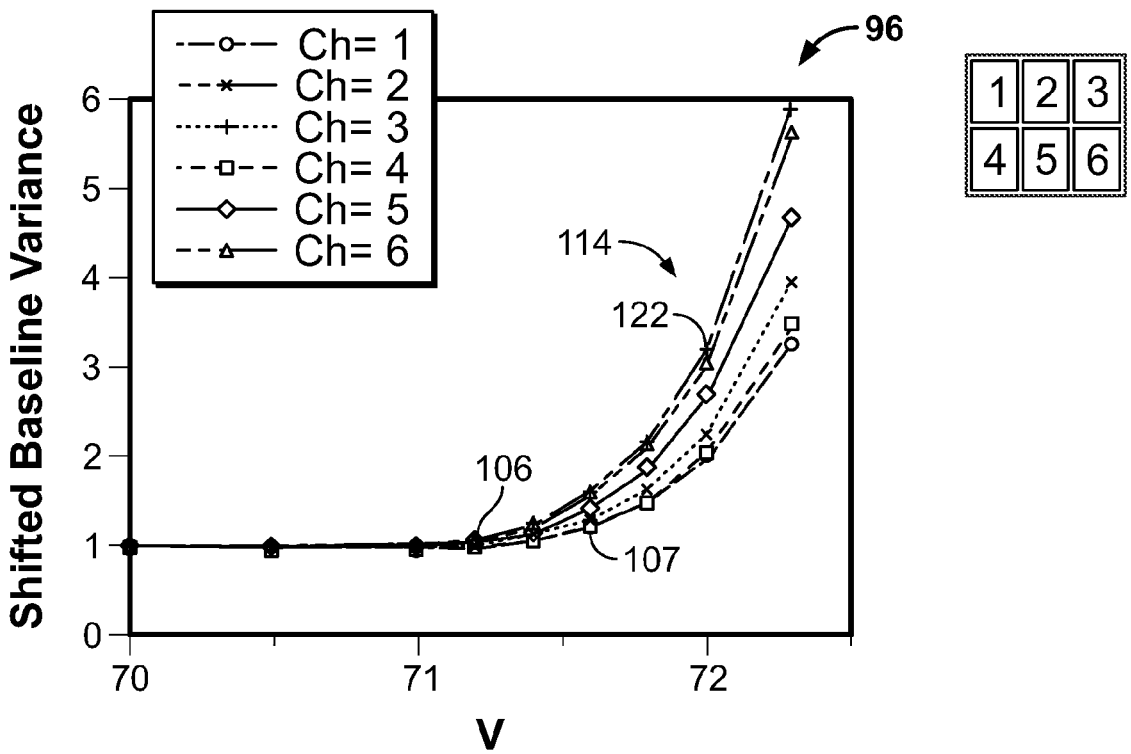

In various embodiments, the current I may be measured as a baseline shift (by digitizing or integrating) of the output signals from the buffer amplifiers 82. It should be noted that the average of a number of random samples of the offset may be used to improve the measurement, which may include any natural or background radiation source as this source amplifies the average measured signal. If a number of random samples of the baseline are measured, the variance of the baseline can be calculated. The change in the variance of the baseline as a function of bias voltage, such as shown in FIGS. 8 and 9, can then be used to determine the breakdown voltage. Thereafter, by extrapolating the I-V curve(s), a breakdown voltage can be measured and the same over-voltages set for each of the SIPMs 62.

In various embodiments, the signal processor 86 includes a field-programmable gate array (FPGA) that may be configured to store calibration records (e.g., one or more calibration measurements) and also may be reprogrammed as needed or desired. Additionally, the FPGA may be used to calculate the breakdown voltage using one or more measured I-V curves. It should be noted that the breakdown voltage may be calculated from I-V curves using any suitable method. It also should be noted that in some embodiments, I-V curves are not generated and processed, instead, a target level for the baseline or the time averaged value of the output signal from the readout electronics is determined, and the bias voltage is swept over the appropriate range to determine the bias voltage value that produces the baseline (or time averaged signal) that is equal to the chosen target. The breakdown voltage can then be determined from this bias voltage value. The various SIPMs 62 in the detector may have different target values. For example, the target value for a SIPM 62 may be equal to a constant greater than 1 times the value of the baseline (or time averaged signal) measured at a very low bias voltage. It also should be noted that the comparison can be done after the output signal from the readout electronics has been digitized, or an analog comparator may be used on the signal before the signal is digitized.

Figure 6:
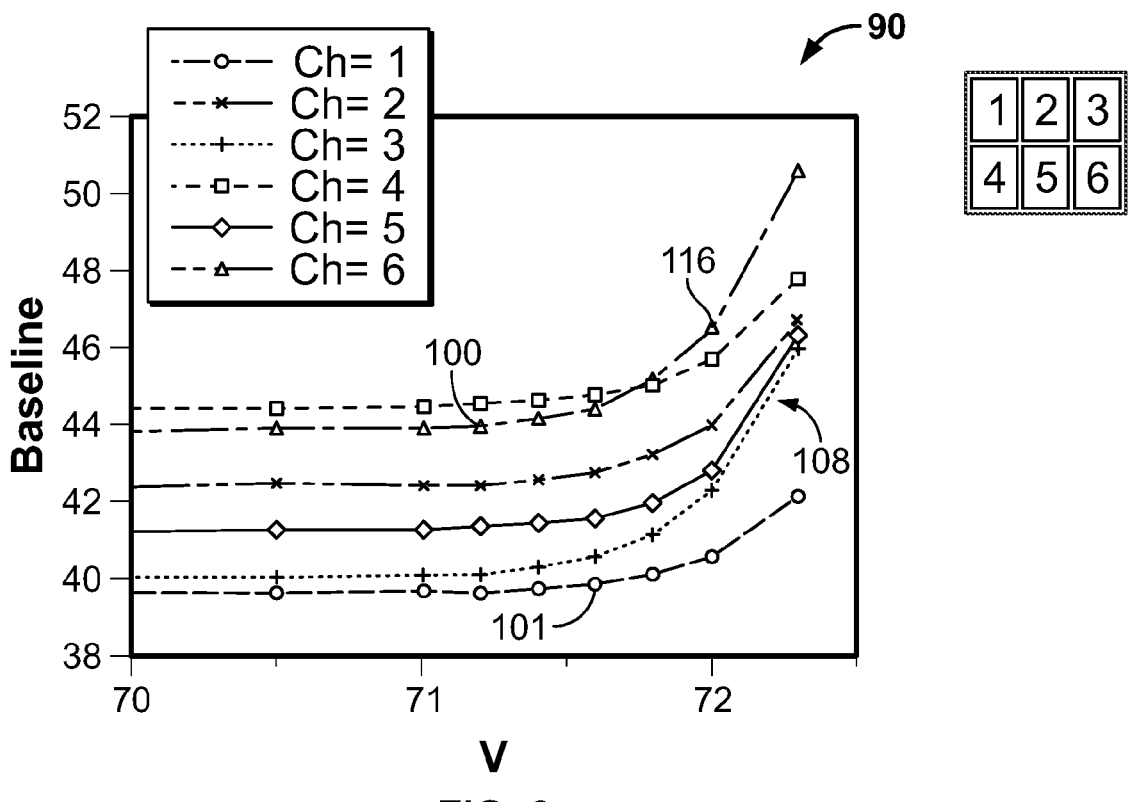
FIGS. 6-9 are graphs of dark currents in accordance with an embodiment.
Figure 7:
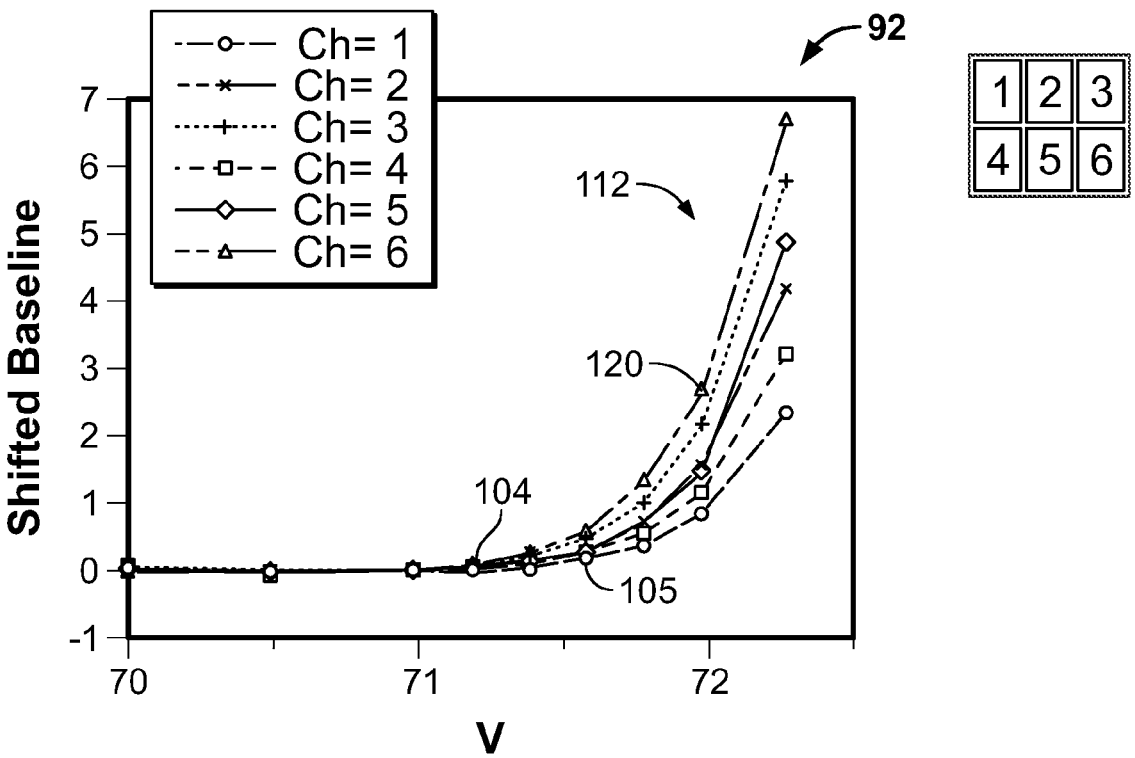

Accordingly, in various embodiments, baseline, time averaged signal, and variance measurements may be used for calibration. For example, FIGS. 6 and 7 illustrate graphs 90 and 92 of the measured baselines versus the overvoltage on the SIPM 62 and baseline curves shifted such that the curves have a value of zero at a bias voltage of 70 volts, respectively. Additionally, FIGS. 8 and 9 illustrate graphs 94 and 96 of the measured baseline variance and the variance normalized to a value of 1 at a bias voltage of 70 volts, respectively. Additionally, FIGS. 6-9 illustrate that the shifted baseline and the normalized baseline variance (as shown in the graphs 94 and 96) generally follow the same trend or curve characteristics. In various embodiments, the transition points 100-107 may be determined using any method that identifies the points at which a curve of the sets of curves 108, 110, 112, 114 changes from generally or substantially flat or horizontal (little or no increase) to curved. That is the first derivative of the curve changes from a value close to 0 to a value that is substantially larger. It should be noted that while the transition points of curves from different anodes (for example, transition points 100 and 101) may occur at different bias voltages, the transition points from the various graphs are substantially the same for a given anode (for example, transition points 100, 102, 104, and 106).

In various embodiments, the transition points may be determined by applying a curve fitting function. In some embodiments, the transition points 100-107 may be identified by determining an increase above a defined value, such as based on a predetermined breakdown current value. For example, in one embodiment, the transition points 100 and 101 are determined as the point on the curves where the baseline value is 20 microamps above the value at a bias value of 70 volts.

It should be noted that in various other embodiments, a different transition point may be used, for example, the transition points 116, 118, 120 and 122 of the set of curves 108, 110, 112, 114, respectively. The transition points 116, 118, 120 and 122 generally correspond to a sharp change in the curvature of the curves 108, 110, 112, 114, such that the curves 108, 110, 112, 114 extend generally or substantially vertically after the transition points 116, 118, 120 and 122. Additionally, a combination of the transition points 100, 102, 104, 106 and the transition points 116, 118, 120 and 122 may be used.

It should be noted that each of the SIPMs 62 may include a plurality of microcells (e.g., 10,000 microcells). Accordingly, for example, measured baseline currents may vary from SIPM 62 to SIPM 62 such as a result of the manufacturing process.

Figure 10:
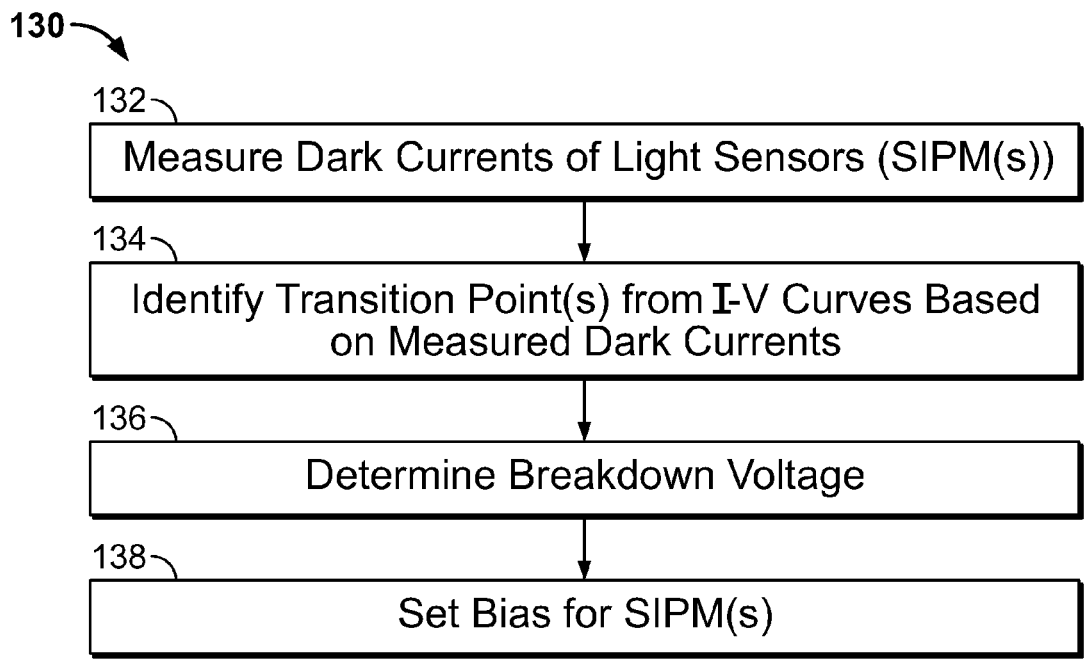
FIG. 10 is a flowchart of a method for calibrating gamma detectors in accordance with various embodiments.

A method 130 for calibrating gamma detectors is shown in FIG. 10. The method 130 includes measuring dark currents of one or more light sensors at 132. For example, in various embodiments, dark currents of one or more SIPMs of the gamma detectors are measured (which may include measured background radiation) as described herein, which may be as a function of bias. Thereafter, at 134, one or more transition points along one or more I-V curves generated based on the measured dark currents is determined. For example, the transition point may be determined as the point where the curve(s) changes from generally horizontal and begins to slope upward or where the curve begins to extend generally vertically. Thus, in various embodiments, a predetermined change in the slope of one or more of the curves may be determined.

Using the determined transition point(s), a breakdown voltage of the SIPMs is determined at 136. For example, the breakdown voltage may be determined based on the measured value at the transition point(s) or a predetermined amount below that point. The determined breakdown voltage is then used to set the bias of the SIPMs at 138 as described herein, for example, at a voltage at a defined amount above the measured voltage at the transition point(s).

Figure 11:
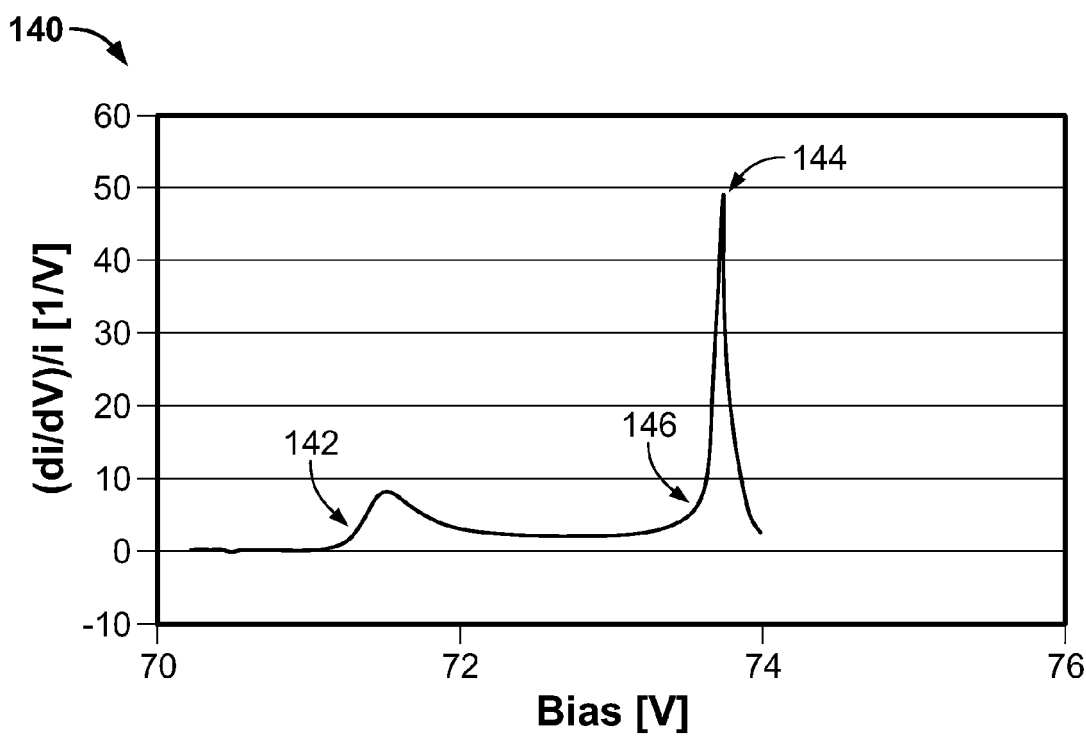
FIG. 11 is a graph of a plot of a normalized rate of dark current versus an applied bias voltage.

Variations and modifications are contemplated. For example, in some embodiments, one or more alternative transition points beyond the first breakdown phenomenon may be used. In particular, the rate of change of the dark current with respect to over-voltage (di/dv) is first obtained to yield the derivative I-V curve, which when further normalized by the dark current (di/dv)/I, provides a standardized measure of the gain change. These alternative transition or transitional points can be used as alternative reference points to set the operating voltage for SIPMs, because these points are at a known offset from the first breakdown point. For example, the graph 140 of FIG. 11 illustrates a plot of a normalized rate of dark current versus applied bias. As can be seen, a first peak 142 is due to avalanche breakdown and a second peak 144 is due mainly to field assisted tunneling. Thus, as can be seen, the onset due to field assisted tunneling after the breakdown pulse (at the first peak 142) is identified at 146. Thus, various embodiments may use alternative transition or transitional points.

Figure 12:
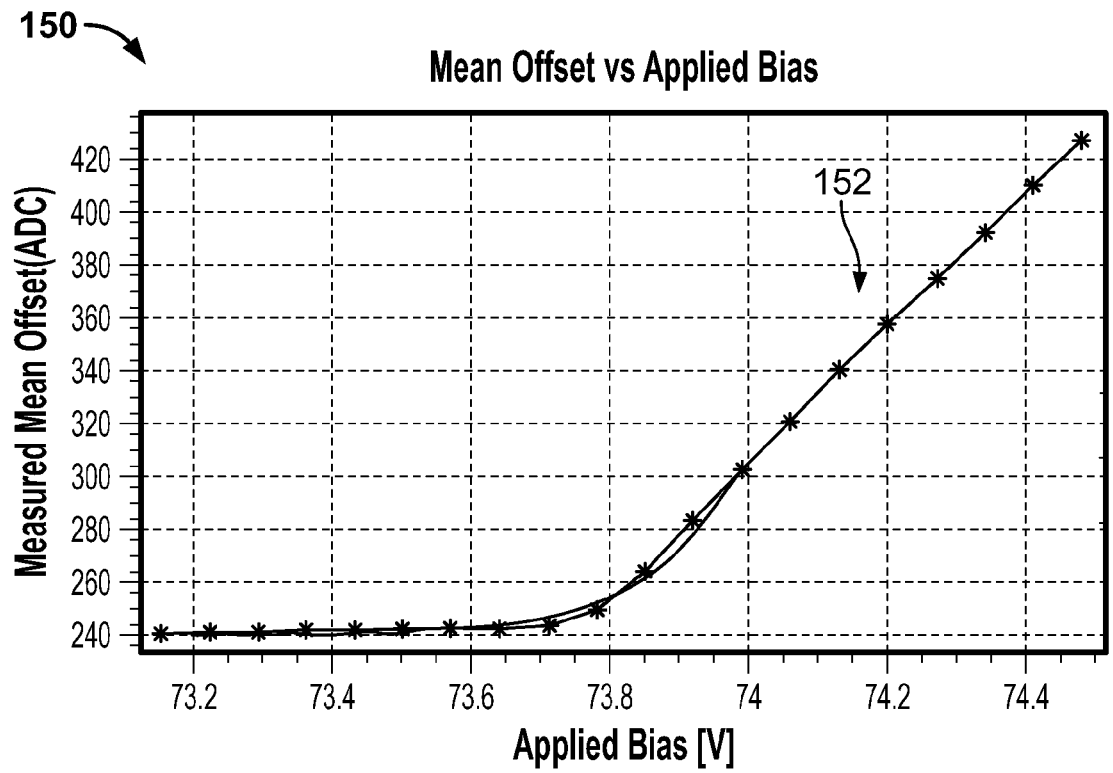
FIG. 12 is a graph of a plot of a measured mean baseline as a function of bias.
Figure 13:
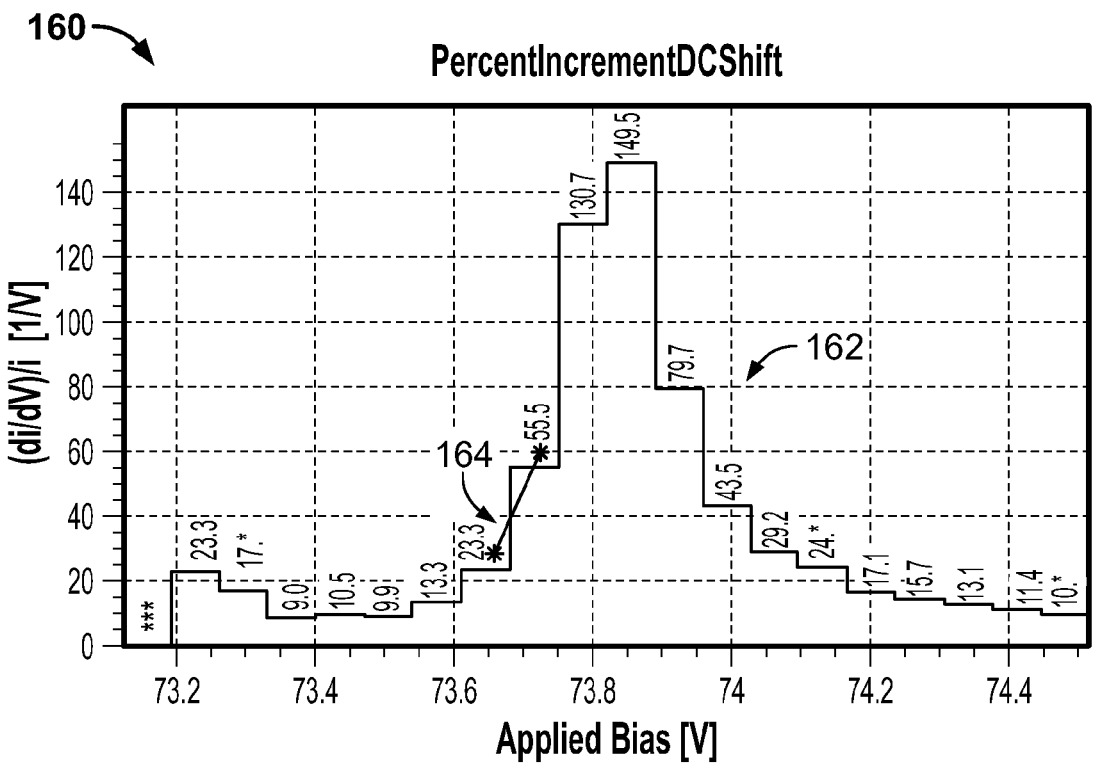
FIG. 13 is a graph of a plot corresponding to a normalized rate of change of dark currents versus bias.

It should be noted that the determination of transition points can be made via a fit of an appropriate model form to the measured data (as shown in FIG. 12) or via an interpolation method of two nearest measured points to a given threshold value (shown in FIG. 13). For example, the graph 150 of FIG. 12 illustrates a plot 152 of a measured mean baseline as a function of bias and the graph 160 of FIG. 13 illustrates a plot 162 corresponding to the normalized change of the dark current versus bias. In various embodiments, the voltage at the onset is determined by interpolation for a threshold, which in the illustrated embodiment is 30 percent (identified by the point 164 in FIG. 13).

In various embodiments, derivative curves, thus, may be obtained and transition points determined. For example, the transition point on a second peak may be measured in addition of a first peak (first breakdown) and used as an alternative reference point.

Thus, in various embodiments, current is measured as a function of applied voltage across each SIPM and the measured relationship analyzed to locate the breakdown voltage for the SIPM. Once the breakdown voltage for each SIPM is known, a fixed offset can be added to set the gain of all the SIPMs to any desired common value. Thus, various embodiments may provide a method of gain calibration for gamma ray detectors, such as gamma ray detectors that use SIPMs. By practicing at least one embodiment, the gains of the SIPMs within a detector block are equalized so that the energy and timing resolution of the detector block is not compromised. Additionally, calibration of each detector block within a PET scanner deployed in the field may be performed even if no prior information about the optimal bias voltages needed to equalize the gains in the SIPM array is provided by the manufacturer of the array. Moreover, in various embodiments, an external calibration source is not used.

Figure 14:
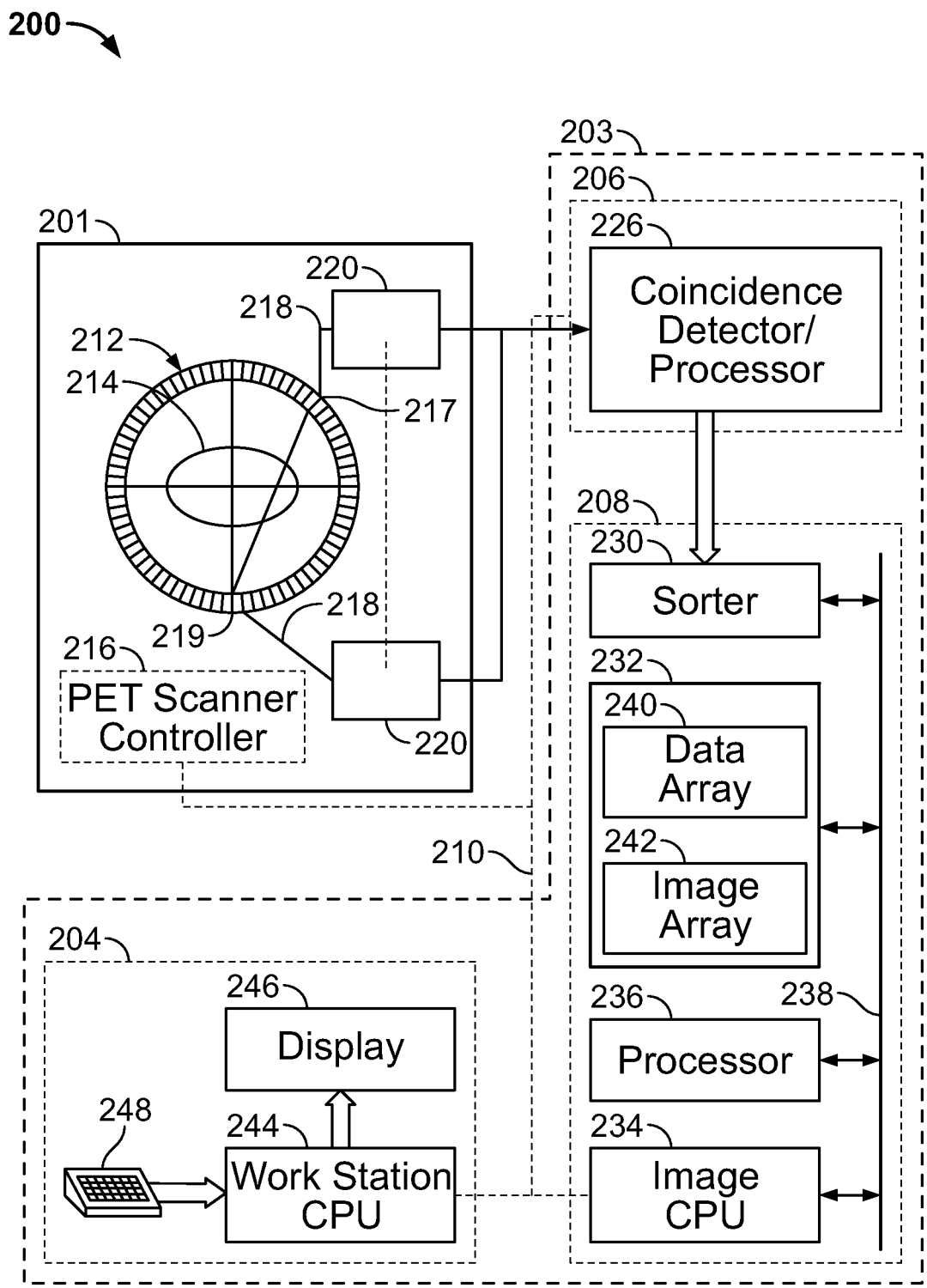
FIG. 14 is a diagram of a PET system in accordance with an embodiment.

FIG. 14 is a block diagram of an exemplary embodiment of a PET system 200 in which various embodiments of the invention may be implemented. The PET system 200 includes a PET scanner 201 and a controller 203 to control image reconstruction processes. The controller 203 is also configured to perform gain calibration as described in more detail herein, which may be performed in part by or be embodied as the gain calibration module 50 (shown in FIG. 1). The controller 203 includes an operator workstation 204 and a processor 205. The processor 205 includes a data acquisition processor 206 and an image reconstruction processor 208. The PET scanner 201, operator workstation 204, data acquisition processor 206 and image reconstruction processor 208 are interconnected via a communication link 210 (e.g., a serial communication or wireless link). The PET scanner 201, which typically includes a gantry (not shown), acquires scan data and transmits the data to the data acquisition processor 206. The operation of the PET scanner 201 is controlled from operator workstation 204. The data acquired by data acquisition processor 206 is reconstructed using image reconstruction processor 208.

The PET scanner 201 may operate, using, for example, a plurality of detector rings. One such detector ring, detector ring 212, is illustrated in FIG. 11, which may be embodied as the detector ring assembly 20 (shown in FIG. 1). The detector ring 212 includes a central opening, in which an object 214 (e.g., a patient) may be positioned, using, for example, a motorized table that is aligned with the central axis of the ring 212. The motorized table moves the object 214 into the central opening of detector the ring 212, in response to one or more commands received from operator workstation 204. A PET scanner controller 216, also referred to as a gantry controller, is provided (e.g., mounted) in the PET scanner 201. The PET scanner controller 216 responds to the commands received from the operator workstation 204 through the communication link 210. Therefore, the operation of the PET scanner 201 is controlled from the operator workstation 204 through the PET scanner controller 216.

The detector ring 212 includes a plurality of detector elements for performing a PET scan of the object 214. For example, there may be 420 crystals per ring and 24 rings in the scanner. As shown in FIG. 11, the detector ring 212 includes a first detector element 217, a second detector element 219, and several other detectors. It should be noted that the detector elements are referred to as the first detector element and the second detector element, only to differentiate location in FIG. 14. The first detector element 217, like the other detectors, includes a set of scintillator crystals arranged in a matrix that is disposed in front of a plurality of photosensors (e.g., the light sensors 34) as described in more detail herein. When a photon collides with a crystal on a detector, the photon produces a scintilla on the crystal. Each photosensor produces an analog signal on the communication line 218 when a scintillation event occurs. A set of acquisition circuits 220 is provided within the PET scanner 201 to receive these analog signals. The acquisition circuits 220 include analog-to-digital converters to digitize analog signals, processing electronics to quantify event signals and a time measurement unit to determine time of events relative to other events in the system. For example, this information indicates when the event took place and the identity of the scintillation crystal that detected the event. The acquisition circuits produce digital data indicating the location, time and total energy of the event. This event data is transmitted through a communication link, for example, a cable, to a coincidence detector or processor 226.

The coincidence detector 226 receives the event data packets from the acquisition circuits 220 and determines if any two of the detected events are in coincidence. In this context, the coincidence is determined by a number of factors. First, the time markers in each event data packet must be within a predetermined time period, for example, 6 ns, of each other. Secondly, the LOR formed by a straight line joining the two detectors that detect the coincidence event should pass through the field of view in PET scanner 201. Events that cannot be paired are discarded. Coincident event pairs are recorded as a coincidence data packet that is communicated through a communication link to a sorter 230 in the image reconstruction processor 208.

The image reconstruction processor 208 includes the sorter 230, a memory module 232, an image CPU 234, an array processor 236, and a back-plane bus 238. The sorter 230 counts all events that occur along each projection ray and organizes them into a coincidence data set. In one embodiment, this data set is organized as a data array 240, referred to as a sinogram. The data array 240 is stored in the memory module 232. The back-plane bus 238 is linked to the communication link 210 through the image CPU 234, which controls communication through the back-plane bus 238. The array processor 236 is also connected to the back-plane bus 238, receives the data array 240 as an input, and reconstructs images in the form of the image arrays 242. The resulting image arrays 242 are stored in the memory module 232.

The images stored in the image array 242 are communicated by the image CPU 234 to the operator workstation 204. The operator workstation 204 includes a CPU 244, a display device 246, and an input device 248. The CPU 244 connects to the communication link 210 and receives inputs (e.g., user commands) from the input device 248, which may be, for example, a keyboard, mouse, or a touch-screen panel. The operator can control the calibration of the PET scanner 201, the configuration of the PET scanner 201, and the positioning of the object 214 for a scan through the input device 248 and associated control panel switches. Similarly, the operator can also control the display of the resulting image on the display device 246 and perform image-enhancement functions, using programs executed by the workstation CPU 244.

The processor 205 is configured to process the scan data received from the detector elements. The scan data includes, for example, sinogram and timing information that is received by processor 205 from the detector elements during an imaging scan. The timing information in one embodiment is the difference in time at which two photons emitted in an annihilation event are detected by detector elements. The timing information may include time stamp information relating to a measured photon event detected by a pair of detector elements, for example, the first detector element 217 and the second detector element 219, for the PET system 200. The time stamp information is the time at which each photon is detected by a detector element, which in various embodiments.

The timing information is received by detectors, which include, for example, a block of 36 scintillator crystals attached to an array of photosensors. The scintillator crystals convert the incoming photon from the patient into a plurality (e.g., several thousand) of light photons (e.g., visible or near UV), which are detected by the photosensors. The proportion of light photons detected by each photosensor channel is used to determine which of the 36 crystals received the incoming photon. The timing signal is determined by processing the leading edge of the signals, to estimate the arrival of the light photons at the light sensors 34 of, for example, the SIPM. This timing signal is then digitized and processed subsequently.

The energy and timing information are used to reconstruct an image of the object 214, scanned by the PET system 200. The reconstruction may include, for example, a two-dimensional or three-dimensional reconstruction. The timing data of each detector element may be configured as a timing bias matrix with a timing recovery value for each set of projection rays of the PET system 200. It should be noted that a detector element pair detects the projection rays from a photon event.

The timing bias data of each detector element pair corresponding to the projection ray is stored in the memory module 232 of the PET system 200.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for calibrating a gamma ray detector, the method comprising:
   measuring signals generated by one or more light sensors of a gamma ray detector;
   generating one or more derived curves using the measured signals as a function of bias voltage;
   identifying a transition point in the one or more derived curves, wherein the transition point corresponds to a switch from a horizontal portion to at least one of a curved portion or a vertical portion;
   determining an onset of a breakdown voltage of the one or more light sensors using the identified transition point; and
   setting a bias of the one or more light sensors at a predetermined value from the determined onset of the determined breakdown voltage.

2. The method of claim 1, wherein the derived curve is the baseline of the measured signal as a function of bias voltage.

3. The method of claim 1, wherein the derived curve is the variance in baseline of the measured signal as a function of bias voltage.

4. The method of claim 1, wherein the derived curve is the time averaged measured signal as a function of bias voltage.

5. The method of claim 1, wherein the transition point is a point along the one or more derived curves where a slope of the curve changes from about horizontal to curved.

6. The method of claim 1, wherein the onset of the breakdown voltage is determined at a predetermined amount below the transition point.

7. The method of claim 1, wherein the one or more derived curves comprise one of a scaled or offset version of I-V curves.

8. The method of claim 1, wherein the transition point is determined by averaging a plurality of transition points in a plurality of derived current curves.

9. The method of claim 1, wherein the transition point is determined as a point at a defined amount above a threshold.

10. The method of claim 1, wherein the one or more light sensors comprise one or more Silicon photomultipliers (SIPMs).

11. The method of claim 1, wherein the measured signals include signals from at least one of a natural background radiation or external radiation source.

12. The method of claim 1, further comprising measuring at least one of a signal baseline value or a time average of the signal height for the one or more light sensors.

13. A non-transitory computer readable storage medium for calibrating a gamma ray detector using a processor, the non-transitory computer readable storage medium including instructions to command the processor to:
measure signals generated by one or more light sensors of a gamma ray detector;
generate one or more derived curves using the measured signals as a function of bias voltage;
identify a transition point in the one or more derived curves, wherein the transition point corresponds to a switch from a horizontal portion to at least one of a curved portion or a vertical portion;
determine an onset of a breakdown voltage of the one or more light sensors using the identified transition point; and
set a bias of the one or more light sensors at a predetermined value from the determined onset of the determined breakdown voltage.

14. The non-transitory computer readable storage medium of claim 13, wherein the transition point is a point along the one or more derived curves where a slope of the curve changes from about horizontal to curved.

15. The non-transitory computer readable storage medium of claim 13, wherein the onset of the breakdown voltage is determined at a predetermined amount below the transition point.

16. The non-transitory computer readable storage medium of claim 13, wherein the one or more derived curves comprise one of a scaled or offset version of I-V curves.

17. The non-transitory computer readable storage medium of claim 13, wherein the transition point is determined by averaging a plurality of transition points in a plurality of derived curves.

18. The non-transitory computer readable storage medium of claim 13, wherein the one or more light sensors comprise one or more Silicon photomultipliers (SIPMs).

19. The non-transitory computer readable storage medium of claim 13, wherein instructions to command the processor to measure at least one of a signal baseline value or a time average of the signal height for the one or more light sensors.

20. A Position Emission Tomography (PET) system comprising:
a plurality of gamma ray detector elements configured to acquire scan data, the detector elements having scintillator crystals with a plurality of light sensors; and
a processor configured to measure signals generated by one or more of the plurality of light sensors of the gamma ray detector, generate one or more derived curves using the measured signals as a function of bias voltage, identify a transition point in the one or more derived curves, wherein the transition point corresponds to a switch from a horizontal portion to at least one of a curved portion or a vertical portion, determine an onset of a breakdown voltage of the one or more of the plurality of light sensors using the identified transition point, and set a bias of one or more of the plurality of light sensors at a predetermined value from the determined onset of the breakdown voltage.

21. The PET system of claim 20, wherein the transition point is a point along the one or more derived curves where a slope of the curve changes from about horizontal to curved.

22. The PET system of claim 20, wherein the onset of the breakdown voltage is determined at a predetermined amount below the transition point.

23. The PET system of claim 20, wherein the one or more derived curves comprise one of a scaled or offset version of I-V curves.

24. The PET system of claim 20, wherein the plurality of light sensors comprise one or more Silicon photomultipliers (SIPMs).

25. The PET system of claim 20, wherein the processor is configured to measure at least one of a signal baseline value or a time average of the signal height for one or more of the plurality of light sensors.

* * * * *